(12) United States Patent
Tornay et al.

(10) Patent No.: US 9,625,455 B2
(45) Date of Patent: Apr. 18, 2017

(54) METHOD AND DEVICE FOR PERFORMING BIOLOGICAL AND/OR CHEMICAL ASSAYS

(71) Applicant: MYCARTIS NV, Zwijnaarde / Ghent (BE)

(72) Inventors: Raphael Tornay, Illarsaz (CH); Nicolas Demierre, Chatel-St-Denis (CH); Jose De Gil, Ecublens (CH); Robin Muller, Estavayer-le-Lac (CH); Didier Falconnet, Ecublens (CH)

(73) Assignee: MYCARTIS NV, Zwijnaarde, Ghent (BE)

( * ) Notice: Subject to any disclaimer, the term of this patent is extended or adjusted under 35 U.S.C. 154(b) by 110 days.

(21) Appl. No.: 14/413,314

(22) PCT Filed: Jul. 10, 2013

(86) PCT No.: PCT/EP2013/064635
§ 371 (c)(1),
(2) Date: Jan. 7, 2015

(87) PCT Pub. No.: WO2014/009446
PCT Pub. Date: Jan. 16, 2014

(65) Prior Publication Data
US 2015/0141281 A1    May 21, 2015

(30) Foreign Application Priority Data
Jul. 11, 2012   (EP) .................................... 12175954

(51) Int. Cl.
*G01N 33/543* (2006.01)
*B01L 3/00* (2006.01)

(52) U.S. Cl.
CPC .. *G01N 33/54313* (2013.01); *B01L 3/502761* (2013.01); *G01N 33/54366* (2013.01);
(Continued)

(58) Field of Classification Search
CPC ....... B01L 2200/0668; B01L 2400/086; B01L 3/502761; G01N 33/543; G01N 33/54313;
(Continued)

(56) References Cited

U.S. PATENT DOCUMENTS

| | | | |
|---|---|---|---|
| 8,124,015 B2* | 2/2012 | Diercks | ............. B01L 3/502761 422/68.1 |
| 2011/0138890 A1* | 6/2011 | Sakamoto | ......... B01L 3/502753 73/61.75 |

FOREIGN PATENT DOCUMENTS

| | | | | |
|---|---|---|---|---|
| EP | 2 336 781 | 6/2011 | ............. | G01N 33/58 |
| WO | WO 00/63695 | 10/2000 | ........... | G01N 33/532 |

(Continued)

OTHER PUBLICATIONS

International Search Report for International Application No. PCT/EP2013/064635, Oct. 16, 2013.

*Primary Examiner* — Maureen Wallenhorst
(74) *Attorney, Agent, or Firm* — Kusner and Jaffe

(57) ABSTRACT

A method for performing a chemical and/or a biological assay including the following successive steps of: a) providing an assay device with a microchannel having an inlet and an outlet and restricting means for restricting movement toward the outlet of microparticles introduced in the microchannel while letting a fluid to flow through the restricting means, b) introducing microparticles in the microchannel via the inlet, c) restricting the movement of said microparticles in the microchannel toward the outlet using the restricting means, d) flowing a fluid sample through the microchannel, and e) performing a biological and/or chemical read-out on each microparticle. The method also includes the steps of: f) moving the microparticles in the microchannel, and g) repeating successively the steps d) and e).

8 Claims, 4 Drawing Sheets

(52) U.S. Cl.
CPC  *G01N 33/54373* (2013.01); *B01L 2200/0668* (2013.01); *B01L 2400/086* (2013.01); *Y10T 436/2575* (2015.01)

(58) Field of Classification Search
CPC ....... G01N 33/54366; G01N 33/54373; G01N 21/64; G01N 21/6428; G01N 21/643; Y10T 436/25; Y10T 436/25375; Y10T 436/2575
USPC ....... 436/148, 164, 165, 172, 174, 177, 180, 436/501, 518; 422/82.08, 502–505, 534; 435/7.1, 287.3, 288.3, 288.4, 288.7; 506/9, 39
See application file for complete search history.

(56) References Cited

FOREIGN PATENT DOCUMENTS

| | | | |
|---|---|---|---|
| WO | WO 2008/063758 | 5/2008 | ............... C12Q 1/00 |
| WO | WO 2010/072011 | 7/2010 | ............... B01L 3/00 |

\* cited by examiner

METHOD AND DEVICE FOR PERFORMING BIOLOGICAL AND/OR CHEMICAL ASSAYS

FIELD OF THE INVENTION

The present invention relates to assay technology in the life science industry and in particular to multiplexing applied in diagnostics, genomic research and molecular biology. The present invention relates in particular to a method for performing biological and/or chemical assays and to an assay device dedicated for this purpose.

BACKGROUND OF THE INVENTION

Within the scope of the present invention, a microcarrier or a microparticle refers to any type of particles, respectively to any type of carriers, microscopic in size, typically with the largest dimension being from 100 nm to 300 micrometers, preferably from 1 µm to 200 µm.

According to the present invention, the term microcarrier refers to a microparticle functionalized, or designed to be functionalized, that is containing, or designed to contain, one or more ligands or functional units bound to the surface of the microcarriers or impregnated in its bulk. A large spectrum of chemical and biological molecules may be attached as ligands to a microcarrier. A microcarrier can have multiple functions and/or ligands. As used herein, the term functional unit is meant to define any species that modifies, attaches to, appends from, coats or is covalently or non-covalently bound to the surface of said microcarrier or impregnated in its bulk. These functions include all functions that are routinely used in high-throughput screening technology and diagnostics.

The term microchannel or microfluidic channel refers to a closed channel, i.e. an elongated passage for fluids, with a cross-section microscopic in size, i.e. with the smallest dimension of the cross-section being typically from about 1 to about 500 micrometers, preferably about 10 to about 300 micrometers. A microfluidic channel has a longitudinal direction, that is not necessarily a straight line, and that corresponds to the direction in which fluids are flowing within the microfluidic channel, i.e. preferably essentially to the direction corresponding to the average speed vector of the fluid, assuming a laminar flow regime.

Drug discovery or screening and DNA sequencing commonly involve performing assays on very large numbers of compounds or molecules. These assays typically include, for instance, screening chemical libraries for compounds of interest or particular target molecules, or testing for chemical and biological interactions of interest between molecules. Those assays often require carrying out thousands of individual chemical and/or biological reactions.

Numerous practical problems arise from the handling of such a large number of individual reactions. The most significant problem is probably the necessity to label and track each individual reaction.

One conventional method of tracking the identity of the reactions is achieved by physically separating each reaction in a microtiter plate (microarray). The use of microtiter plate, however, carries several disadvantages like, in particular, a physical limitation to the size of microtiter plate used, and thus to the number of different reactions that may be carried out on the plate.

In light of the limitations in the use of microarray, they are nowadays advantageously replaced by functionalized encoded microparticles to perform chemical and/or biological assays. Each functionalized encoded microparticle is provided with a code that uniquely identifies the particular ligand(s) bound to its surface. The use of such functionalized encoded microparticles allows for random processing, which means that thousands of uniquely functionalized encoded microparticles may all be mixed and subjected to an assay simultaneously. Examples of functionalized encoded microparticles are described in the international patent application WO 00/63695.

The applicant proposed in its international patent application WO 2010/072011 an assay device having at least one microchannel with an inlet and an outlet, the microchannel serving as a reaction chamber in which a plurality of functionalized encoded microparticles or microcarriers 10 (FIG. 1) can be packed. The microfluidic channel is provided with restricting or stopping means acting as a filter that allows a liquid solution containing chemical and/or biological reagents to flow through while blocking the microcarriers 10 inside the microchannel. The microparticles 10 are designed such that their shape and size relative to the cross-section of the microchannel prevent any overlapping of adjacent microcarriers 10. Thus, the microcarriers 10 exhibit a monolayer arrangement inside each microchannel and are stacked onto the restricting means along the microchannel.

Those functionalized encoded microcarriers 10 that show a favorable reaction of interest between their attached ligand(s) and the chemical and/or biological reagents flowing through may then have their code optically read, thereby leading to the identification of the ligand producing the favorable reaction.

The code may comprise a distinctive pattern of a plurality of traversing holes 12 and may also include an asymmetric orientation mark such as, for example, a L-shaped sign 14 (as shown in FIG. 1) or a triangle. This asymmetric orientation mark allows the distinction between the top surface 16 and the bottom surface 18 of the microcarrier 1.

With the assay device described in WO 2010/072011, microparticles are introduced within the microchannel from the inlet and immobilized onto the restricting means. Then, a biological sample (comprising one or more target molecules) is flown in the microchannel (comprising one or more sets of microcarriers) around the microparticles and then through the restricting means toward the outlet, the microcarriers being still blocked by the restricting means. The detection of a reaction of interest can be based on continuous readout of the fluorescence intensity of each encoded microcarrier present in a microfluidic channel. In other words, the presence of a target molecule in the assay will trigger a predetermined fluorescent signal.

However, after the microparticles 10 have been inserted within the microchannel and are stacked onto the restricting means, the microparticles 10 may be slightly offset relative to one another in the direction perpendicular to the microchannel 20, i.e. in the Z-direction (FIG. 2).

Then, when performing the continuous read-out of fluorescence as described in WO2010/072011A1, it has then been observed that some or all of the microparticles 22 may exhibit a non-homogenous intensity over their surface emitting fluorescence light in response to binding of target molecules (FIG. 3).

FIG. 4 is an enlarged view of a microparticle 22 presenting a non-homogenous intensity over its surface. The microparticle 22 clearly exhibits one region 24 having a grey level inferior to a second surrounding region 26.

This non-homogenous intensity is due to non-homogeneous mass transfer in the microchannel which is mainly the consequence of the particular arrangement of microcarriers 10 in the Z-direction within the microchannel 20. Non-homogeneous mass transfer within the microchannel 20 leads to a non-uniform flow of the target molecules on the surface of the microparticles.

The non-homogeneous mass transfer is problematic as it affects the attribution of the fluorescence value to the microcarrier. In case non-homogeneity is significant, the value of fluorescence that is attributed to the microcarrier will not reflect the correct concentration of target molecules within the analyzed sample.

Thus, non-homogeneous mass transfer affects the reliability of the measured signal. Incorrect values on a plurality of microcarriers can lead to serious consequences on the reliability of the assay and therefore on its usefulness in the field of diagnostics, genomic research and molecular biology.

SUMMARY OF THE INVENTION

The present invention aims to remedy all or part of the disadvantages mentioned above.

To this aim, the invention proposes a method for performing a chemical and/or a biological assay comprising at least the following successive steps of:
a) providing an assay device comprising at least one microchannel having at least an inlet and at least an outlet, said assay device further comprising restricting means designed to restrict the movement toward the outlet of microparticles introduced in the microchannel while letting a fluid to flow through the restricting means toward the outlet,
b) introducing a plurality of microparticles in the microchannel via the inlet, each microparticle having a shape relative to the cross-section of the microchannel that prevents overlapping of two adjacent microparticles,
c) restricting the movement of said microparticles in the microchannel toward the outlet using restricting means,
d) flowing a fluid sample through the microchannel,
e) performing a biological and/or chemical read-out on each microparticle, the method further comprising the steps of:
f) moving the microparticles in the microchannel while the movement of the microparticles toward the outlet is still restricted by said restricting means and,
g) repeating successively the steps d) and e).

Thus, in the method according to the invention, the microparticles are moved between two successive biological and/or chemical read-outs in order to at least modify the arrangement of the microparticles relative to each other in the direction perpendicular to the microchannel so as to reduce the effect of non-homogeneous mass transfer as described above.

Indeed, when performing a first biological and/or chemical read-out, particular distribution of mass transfer may establish within the microchannel depending on the microparticles arrangement within the microchannel, thereby creating flow patterns on the microcarriers. However, moving the microparticles before performing a second biological and/or chemical read-out induces a change in the distribution of mass transfer within the microchannel. Thus, inhomogeneities of intensity due to non-homogeneous mass transfer are statistically averaged over time on all the microparticles leading to an homogenous intensity collected on each microparticle over time.

It is then possible to follow in a reliable manner a kinetic reaction by making read-outs at different time points.

According to another feature of the invention, the steps f to g are repeated at least one time after the end of the step g, thus allowing a change of the distribution of mass transfer several times during biological and/or chemical interactions of target molecules with the microparticles.

Preferentially, the steps f to g are repeated at least at a given frequency, thus allowing a regularly random redistribution of microcarriers in the microchannel throughout the biological and/or chemical assay over time.

In a particular embodiment of the invention, the given frequency is comprised in a range from 0.05 Hz to 1 Hz and more preferentially is in comprised in a range from 0.5 Hz to 2 Hz.

According to another feature of the invention, the step f) consisting in moving the microparticles within the microchannel is performed for a first given period which is long enough to induce a change in the distribution of mass transfer in the microchannel.

It should also be understood that this first period should be determined in such a way not to increase the time required for performing a complete biological and/or chemical assay.

In an embodiment of the invention, the first given period is comprised within a range from 0.5 to 5 seconds. This period has been found to meet a good compromise between the time required for performing the complete assay and the need to sufficiently move the microparticles so as to induce a change in the distribution of mass transfer.

According to another feature of the invention, the step g is performed for a second given period.

The second given period insures that all microparticles have enough time to interact with reagents and target molecules present in the fluid sample and that the detection of the signal emitted from the microparticles is carried out. Thus, this second desired period is a key feature to obtain a good mass transfer of the target molecules on the microparticles.

In an embodiment of the invention, the second given period is comprised within a range from 0.2 to 5 seconds.

According to another embodiment of the invention, the step f) consists in moving the microparticles backward and then forward along the microchannel so as to spatially and randomly rearrange the microparticles relative to one another along the microchannel, thus leading to modify the distribution of mass transfer that may have built up within the microchannel.

In a particular embodiment of the invention, the microparticles are moved backward by applying a negative differential pressure of fluid sample between the inlet and outlet of the microchannel and moved forward by applying a positive differential pressure of fluid sample between the inlet and outlet of the microchannel. In an embodiment, the negative differential pressure is comprised between −20 and −200 mbars. According to the invention, the positive differential pressure is comprised between 20 and 200 mbars.

In another embodiment of the invention, the microparticles are moved backward by applying a displacement of fluid sample by mechanical actuation from the outlet to the inlet of the microchannel and moved forward by applying a displacement of fluid sample by mechanical actuation from the inlet to the outlet of the microchannel. Advantageously the mechanical actuation is obtained by connecting a syringe pump to the microchannel and moving the syringe piston.

Preferentially, in step f) the microparticles are moved toward the inlet of the microchannel on a distance representing at least 5 times the dimension of a microparticle measured along the microchannel.

This value has been found to correspond to the optimal distance over which the microparticles should be moved so as guarantee a random rearrangement of the microparticles relative to one another within the microchannel, leading to a random change of the distribution of mass transfer within the microchannel.

According to an embodiment of the invention, a step f' is implemented between the step f and the step g and consists in moving the microparticles toward the outlet until their movement is restricted by the restricting means.

Moving the microparticles toward the outlet until their movement is restricted by the restricting means provides a static configuration of the microparticles for performing the assay and readout in which the microparticles are always located at a same region within the microchannel.

The invention also relates to an assay device for performing the method according to the invention and comprising at least one microchannel having at least an inlet and an outlet, said microchannel being designed to accommodate a plurality of microparticles, characterized in that the inlet and the outlet are connected to pressure applying means linked to control means for controlling pressure applying means so as to generate negative and positive differential pressure between inlet and outlet.

The assay device according to the invention allows moving backward and forward microparticles inserted within a microchannel by varying the differential pressure applied to the inlet and the outlet of the microchannel, thus allowing preventing or at least reducing the effect of non-homogeneous mass transfer on a biological and/or chemical assay.

BRIEF DESCRIPTION OF THE DRAWINGS

The invention can be better understood and other details, features, and advantages of the invention appear on reading the following description made by way of non-limiting examples with reference to the accompanying drawings, in which.

DETAILED DESCRIPTION OF THE INVENTION

Figure 1:
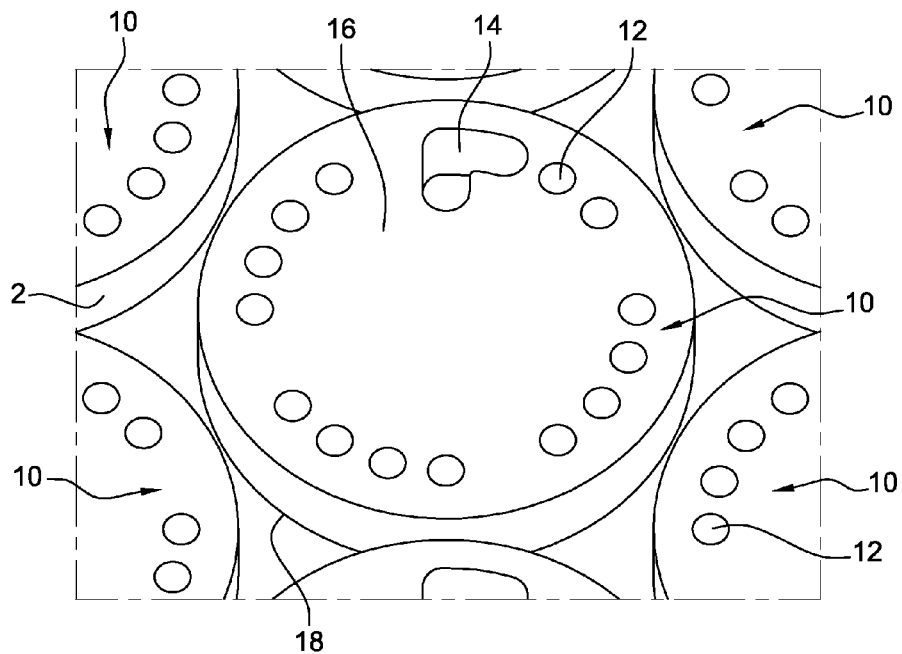
FIG. 1 illustrates a top perspective view of a microcarriers according to the prior art.
Figure 2:
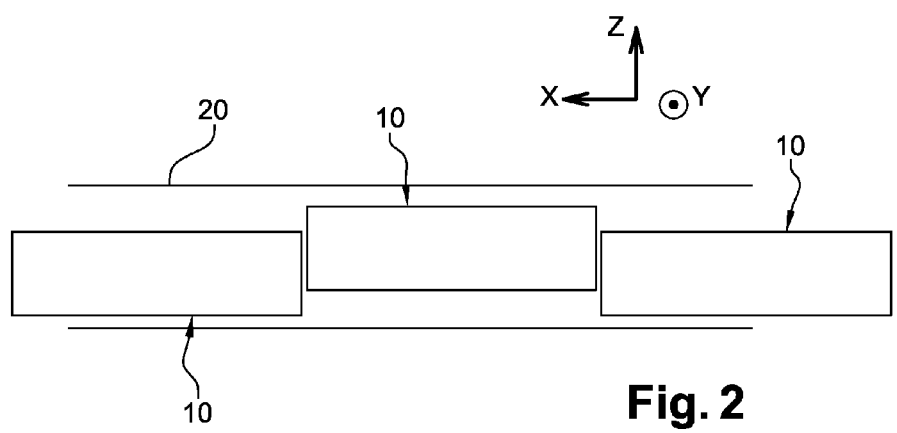
FIG. 2 illustrates the positioning of microcarriers relative to one another within a microchannel.
Figure 3:
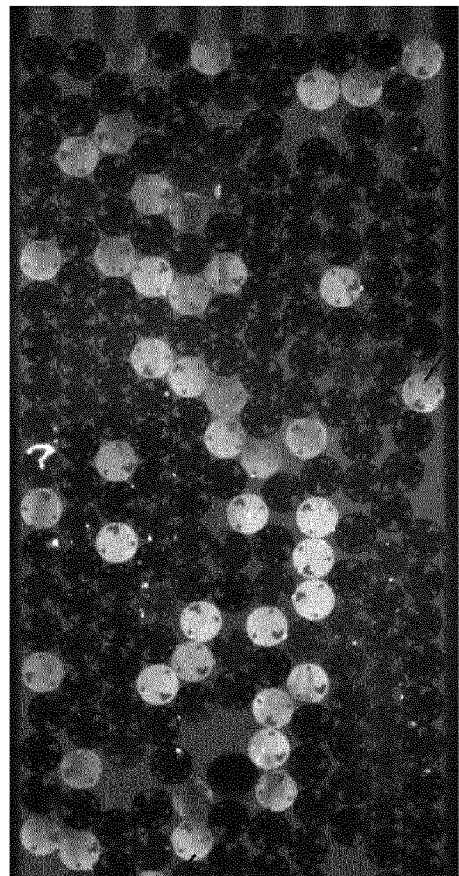
FIG. 3 is an image of the fluorescence obtained with a method and assay device according to the prior art.
Figure 4:
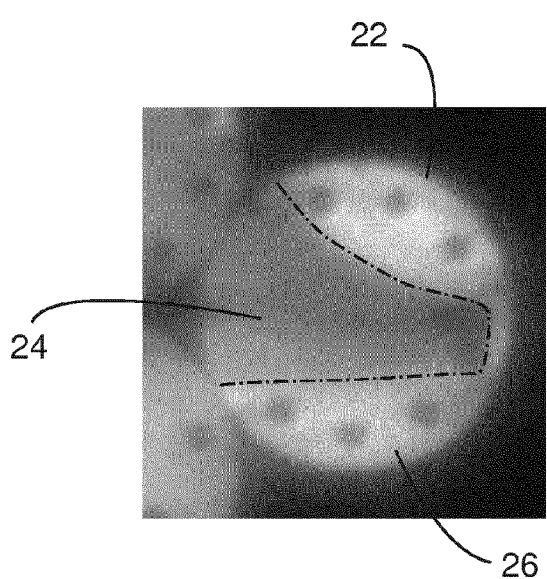
FIG. 4 is an enlarged view of the fluorescence collected from one microcarrier.
Figure 5:
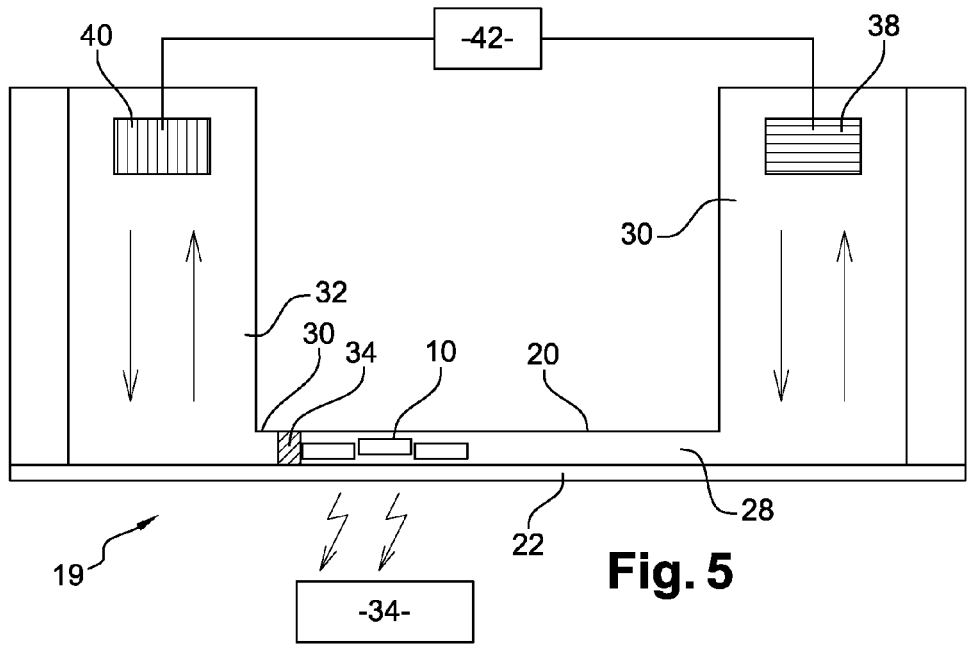
FIG. 5 is a cross sectional view of an assay device according to the invention.

We first refer to FIG. 5 representing an assay device 19 of the present invention and comprising several microchannels 20 (only one is visible on the cross sectional view) formed in a plate 22 and arranged side by side relative to one another. Each microchannel 20 comprises an inlet 28 in fluid communication with an inlet well 30 and an outlet 32 in fluid communication with an outlet well 32.

Each microchannel 20 ends with restricting or stopping means 34 acting as a filter that allows a liquid solution to flow through while blocking the microcarriers 10 inside the microchannel 20.

As mentioned above, the microparticles 10 exhibit a monolayer arrangement inside each microchannel and are stacked onto the restricting means along the microchannel.

The assay device comprises detecting means 36 designed to detect fluorescent signals emitted at the surface of the microparticles 10 in a direction substantially perpendicular to the plate which is optically transparent so that the signal is detectable from the outside of the microchannel.

A first micropump 38 is mounted at the entry of the inlet well 30 and a second micropump 40 is mounted at the exit of the outlet well 32. Both the first and the second micropumps 38, 40 are linked to control means 42 controlling simultaneously the first and second micropumps 38, 40 and thus the differential pressure $\Delta P$ applied to the fluid within the microchannel 20 between the inlet 28 and the outlet 30.

According to the method of the invention, the first step a consists in providing the assay device 19 describes here above.

Figure 6A:
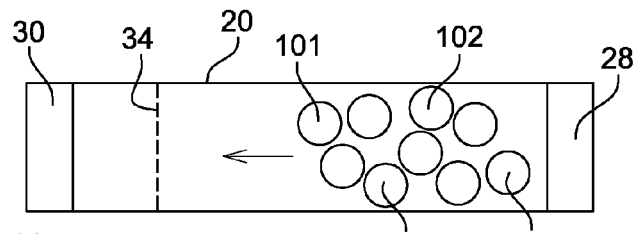
FIGS. 6A, 6B, 6C and 6D are diagrammatic views of different steps of moving the microparticles within the microchannel with the method according to the invention.

A second step b, shown in FIG. 6A, consists in introducing a plurality of microparticles 101, 102, 103, 104 within the inlet well and then in the microchannel. To facilitate the introduction of the microparticles 101, 102, 103, 104 inside the microchannel, the microparticles 101, 102, 103, 104 are beforehand put in solution which is then introduced within the inlet well 30 and the microchannel 20.

In order for the microparticles 101, 102, 103, 104 to flow toward the outlet 30 of the microchannel 20, controlling means 42 control the first and the second pumps 38, 40 so as to generate a positive differential pressure $\Delta P$ between the inlet 28 and the outlet 30 of the microchannel 20.

Figure 6B:
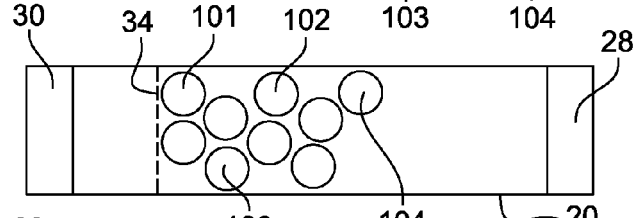

In a third step c, shown in FIG. 6B, the movement of the microparticles 101, 102, 103, 104 toward the outlet of the microchannel 20 is restricted by the restricting means 34.

In a fourth step d, a fluid sample is flown in the microchannel 20 from the inlet 28 toward the outlet 30. The fluid sample comprises all necessary reagents, target and/or non-target molecules to perform the biological assay.

A fifth step e consists in collecting fluorescent signals emitted by the microparticles using the detecting means 34.

Figure 6C:
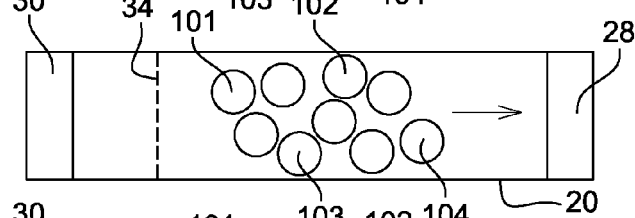

A sixth step f consists in moving the microparticles 101, 102, 103, 104 backward toward the inlet in the microchannel 20, FIG. 6C, and then forward toward the outlet 30 until their movement is restricted by the restricted means 34.

The backward movement (FIG. 6C) of the microparticles 101, 102, 103, 104 is induced by control means 42 controlling the first and second micropumps 38, 40 so as to change the differential pressure between the inlet 28 and the outlet 30 of the microchannel 20 from positive to negative. The forward movement of the microparticles 101, 102, 103, 104 is induced by resetting a positive differential pressure between inlet 28 and outlet 30 of the microchannel 20.

The microparticles 101, 102, 103, 104 are displaced toward the inlet 28 of the microchannel 20 on a distance representing at least 5 times the dimension of the microparticle measured along the microchannel, i.e. 5 times the diameter of the microparticles.

The microparticles 101, 102, 103, 104 are preferably moved backward during a period of time comprised within a range from 1 to 5 seconds in order to guarantee that all microparticles 101, 102, 103, 104 have enough time to move along the microchannel.

Figure 6D:
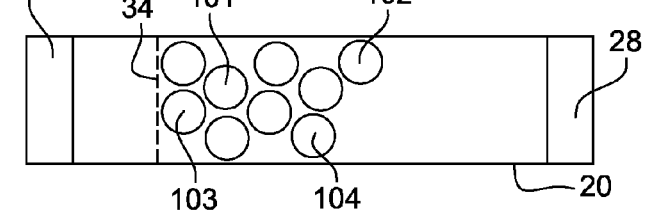

As represented in FIG. 6D, the microparticles 101, 102, 103, 104 have a different spatial arrangement relative to one another along the microchannel 20 as compared to the arrangement observed in FIG. 6B. Then, this change in the spatial arrangement of the microparticles 101, 102, 103, 104 allows a change in the distribution of mass transfer between successive biological and or/chemical read-outs.

In a last step g, the method according to the invention consists in repeating successively the steps d and e during a period of time within a range from 0.2 to 5 seconds.

In a particular embodiment of the method according to the invention, the steps f an g are periodically repeated at a predetermined frequency ranging for example from 0.05 Hz to 5 Hz, in order to regularly modify the distribution of mass transfer in the microchannel 20 during a chemical and/or biological assay.

Figure 7:
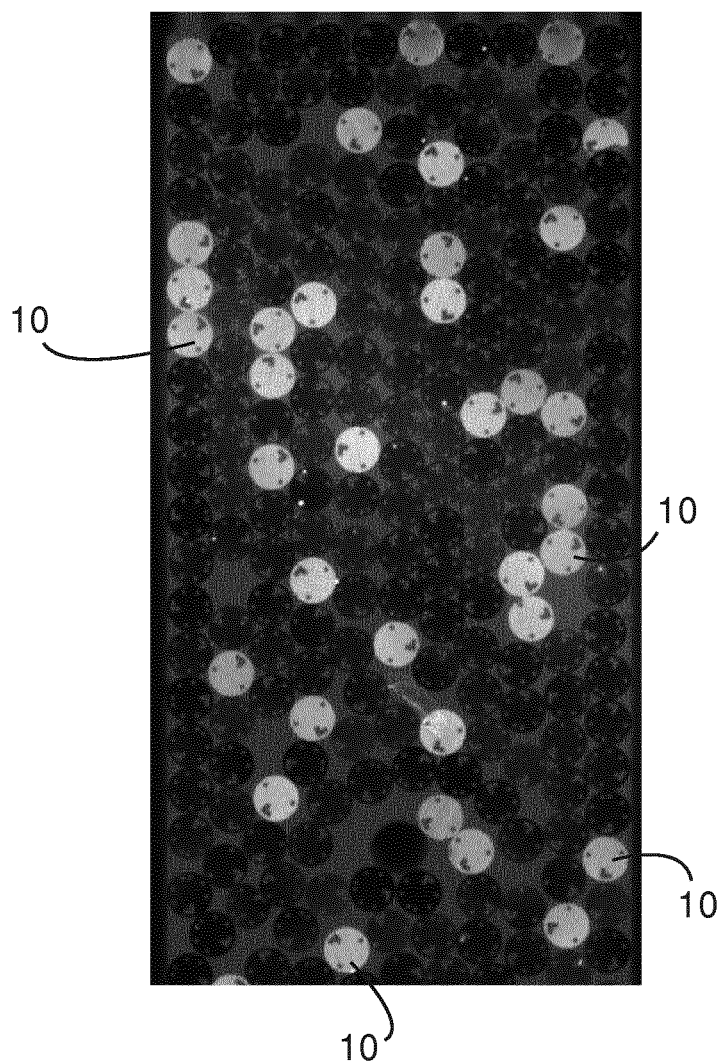
FIG. 7 is an image of the fluorescence obtained with the method according to the invention.

FIG. 7 shows an image of the fluorescence emitted by the microparticles 10. The microparticles having attached ligands which have reacted with chemical and/or biological reagents in the sample solution exhibit an homogenous intensity over their entire surface. Thus, the method according to the invention allows eliminating the effect of non-homogeneous mass transfer on the fluorescence signals collected from the microparticles.

Control means 42 controlling the first and the second micropumps 38, 40 are configured so that each micropump 38, 40 applies to the inlet 28 and the outlet 30 of the microchannel 20 a pressure $P_{inlet}$ and $P_{outlet}$, respectively, higher than the atmospheric pressure $P_{atm}$.

Furthermore, the pressure $P_{inlet}$ and the pressure $P_{outlet}$ together with the absolute variation of the differential pressure $|\Delta P|$ between inlet 28 and outlet 30 of the microchannel are such that $P_{inlet}-|\Delta P|$ and $P_{outlet}-|\Delta P|$ always remains higher than a predetermined pressure so as to prevent the formation of microbubbles within the microchannel 20 that could partially block the microchannel.

In an embodiment of the invention, the pressure $P_{inlet}$ and the pressure $P_{outlet}$ are set to a same value $P_1$.

Non limiting examples of restricting means 34 include a grid, a wire, a mesh filter, a weir construct, one or more pillars extending substantially perpendicularly to the plate, a reduction of the section of the microchannel. An electrostatic or dielectrophoretic force or a magnetic field may be used to immobilize the microparticles. Numerous examples of restricting means are indicated in the patent application WO 2010/072011 of the applicant.

It is also possible to move backward the microparticles 10 by means other than varying the differential pressure as mentioned above. In particular, it would be possible to use magnetic means generating a magnetic field interacting with microparticles 10 sensitive to a magnetic field.

The microparticles 10 are preferably shaped in the form of a disk and have a diameter between 1 and 200 μm, for example 40 μm. The microparticles may also have a different form such as a quadrate or a hexagon.

Other embodiments of the invention will be apparent to those skilled in the art from consideration of the specification and practice of the invention disclosed herein. It is intended that the specification and example be considered as exemplary only, with the true scope and spirit of the invention being indicated by the following claims.

Having described the invention, the following is claimed:

1. A method for performing a chemical and/or a biological assay comprising at least the following successive steps of:

a) providing an assay device comprising (i) at least one microchannel having at least an inlet and at least an outlet, and (ii) restricting means for restricting movement in a direction toward the outlet of microparticles introduced in the microchannel while letting a fluid to flow through the restricting means toward the outlet, b) introducing a plurality of microparticles in the microchannel via the inlet, each microparticle having a shape relative to a cross-section of the microchannel that prevents overlapping of two adjacent microparticles, wherein the microparticles have a dimension d measured along the microchannel, c) restricting the movement of said microparticles in the microchannel toward the outlet using the restricting means, d) flowing a fluid sample through the microchannel, e) performing a biological and/or chemical read-out on each microparticle, said read-out including detection of a signal emitted in association with the biological and/or the chemical assay, f) moving the microparticles (i) backward toward the inlet along the microchannel and (ii) forward toward the outlet along the microchannel, while the restricting means restricts movement of the microparticles in a direction toward the outlet, the backward and forward movement of the microparticles causing spatial and random rearrangement of the microparticles relative to one another along the microchannel, wherein the microparticles are moved toward the inlet of the microchannel a distance representing at least five times the dimension d, and g) repeating successively the steps d) and e), wherein the steps f) and g) are periodically repeated at a predetermined frequency in a range from 0.05 Hz to 5 Hz.

2. The method according to claim 1, wherein the said predetermined frequency is in a range from 0.05 Hz to 1 Hz.

3. The method according to claim 1, wherein the step f) is performed for a first given period.

4. The method according to claim 3, wherein the said first period is within a range from 1 to 5 seconds.

5. The method according to claim 1, wherein the step g) is performed for a second given period.

6. The method according to claim 5, wherein the second period is within a range from 0.5 to 5 seconds.

7. The method according to claim 1, wherein during step f) the microparticles are moved backward by applying a negative differential pressure of fluid ($\Delta P$) sample between the inlet and the outlet of the microchannel and moved forward by applying a positive differential pressure ($\Delta P$) of fluid sample between the inlet and the outlet of the microchannel.

8. The method according to claim 1, further comprising a step f') implemented between the step f) and the step g), said step f') including moving the microparticles toward the outlet until their movement is restricted by the restricting means.

* * * * *